United States Patent
Näslund

[19]
[11] Patent Number: 5,983,424
[45] Date of Patent: Nov. 16, 1999

[54] DEVICE FOR REPOSITIONING A PATIENT

[75] Inventor: Ingemar Näslund, Huddinge, Sweden

[73] Assignee: Elekta AB, Stockholm, Sweden

[21] Appl. No.: 09/068,648

[22] PCT Filed: Nov. 12, 1996

[86] PCT No.: PCT/SE96/01457

§ 371 Date: Jun. 3, 1998

§ 102(e) Date: Jun. 3, 1998

[87] PCT Pub. No.: WO97/17896

PCT Pub. Date: May 22, 1997

[30] Foreign Application Priority Data

Nov. 14, 1995 [SE] Sweden ................................... 9504048

[51] Int. Cl.$^6$ ............................. A47B 13/00; A47B 7/00; A47B 1/00; A61G 7/08

[52] U.S. Cl. .................................. 5/601; 5/81.1 R; 5/628; 5/621

[58] Field of Search .................................... 5/601, 81.1 R, 5/83.1, 86.1, 84.1, 610, 625, 626, 627, 628, 621, 622, 623, 624; 378/209

[56] References Cited

U.S. PATENT DOCUMENTS

| | | | |
|---|---|---|---|
| 1,925,425 | 9/1933 | Wilent | 378/179 |
| 3,293,667 | 12/1966 | Ohrberg | 5/610 |
| 3,609,778 | 10/1971 | Zeiner | 5/628 |
| 3,873,841 | 3/1975 | Cabansag | 5/601 X |
| 3,973,126 | 8/1976 | Redington et al. | 5/601 X |
| 4,015,836 | 4/1977 | Redington et al. | 269/322 |
| 4,033,000 | 7/1977 | Bonifay | 5/628 |
| 4,151,842 | 5/1979 | Miller | 5/628 X |
| 4,779,858 | 10/1988 | Saussereau | 5/601 |
| 5,179,746 | 1/1993 | Rogers | 5/625 |
| 5,201,089 | 4/1993 | Ferreira | 5/627 |
| 5,499,415 | 3/1996 | McKenna | 5/601 |
| 5,572,569 | 11/1996 | Benoit et al. | 5/601 X |
| 5,681,326 | 10/1997 | Lax . | |
| 5,790,996 | 8/1998 | Narfstrom | 5/610 X |
| 5,825,843 | 10/1998 | Kobayashi | 378/209 X |

FOREIGN PATENT DOCUMENTS

| | | |
|---|---|---|
| 2 377 795 | 8/1998 | France . |
| 9302066-7 | 12/1994 | Sweden . |
| 502723 | 12/1995 | Sweden . |
| 2 038 150 | 7/1980 | United Kingdom . |
| WO94/28817 | 12/1994 | WIPO . |

*Primary Examiner*—Terry Lee Melius
*Assistant Examiner*—James M. Hewitt
*Attorney, Agent, or Firm*—Burns, Doane, Swecker & Mathis, L.L.P.

[57] ABSTRACT

A device of high accuracy for repositioning a patient's skeleton and the area in the patient's body which is to be subjected to treatment, the position of the area in relation to the device being previously determined, for instance by angiogram, PET, DSA, CT, MRI or X-ray equipment with the same device. The device includes a non-yielding, upright and radiolucent panel element and a base plate, which in a substantially perpendicular fashion is fixedly connected to panel element, of which at least the panel element includes a fixation arrangement for fixing the patient in a given, essentially upright orientation to the panel element, and that the device also includes one or more wheels mounted on the base plate for moving the panel element and the patient to a radiotherapy table, a tilting and conveying assembly being arranged at the end of the table for tilting the panel element together with the patient from the upright orientation to a lying orientation and conveying these to a defined place on the table.

18 Claims, 3 Drawing Sheets

DEVICE FOR REPOSITIONING A PATIENT

BACKGROUND AND SUMMARY

The present invention relates to a device for repositioning with high accuracy a patient's skeleton and the area in the patient's body that is to be subjected to treatment, the position of the area being previously determined, for example by means of angiogram, PET, DSA, CT, MRI or X-ray equipment.

In radiotherapy as well as in surgical operations, the possibility of identifying the target area with great accuracy is highly important. To minimize the risk, the surgeon must be sure of hitting the correct area in the treatment.

It is vital that the treatment area can be easily and safely identified on different occasions, since, for example, fractionated radiation treatment requires a number of successive treatment sessions.

In radiation treatment of cancer, the intended tumor dose is given as repeated small radiotherapy doses during several weeks. It is thus important that in each treatment session the tumor in the patient is correctly positioned relative to the radiation field of the radiotherapy apparatus.

The prevalent method for positioning a patient's skeleton (body) is that the skin of the part of the body that is to be subjected to radiotherapy is marked with a felt-tip pen, with or without supplementary tattoo points. By means of skin marks and laser position beams, the nurse oncologist tries to arrange the patient in the correct position on the radiotherapy table in each treatment session. There is a drawback of the skin as outer reference for the tumor lying inside the body. The skin is elastic and moves freely relative to the parts of the skeleton. The movement of the skin with the uncertain position of the skin marks in relation to the parts of the skeleton makes it necessary to use safety margins on the radiation fields such that the tumor is not positioned outside the radiation field during treatment. The increased sizes of the fields result in normal tissues without cancer being unnecessarily irradiated. This causes higher radiation energy to the body and may lead to undesired side-effects of the radiotherapy. By irradiating greater volumes than necessary, the total radiation dose cannot in certain positions be increased to the desired level. It is desirable that adjustments of the patient's position on the radiotherapy table can be made more exactly.

A plurality of equipment and techniques are available to reduce deviations in the positioning of a patient, so-called fixtures such as masks, bite blocks, straps, plastic shells etc. The fixation aids should be usable in connection with the computerised axial tomography, the simulator and in the therapy room without affecting the levelling base or the radiotherapy. The problem with the fixation aids is that the patient who lies down in a fixture may on his own lie with his skeleton parts rotating in his own subcutaneous fat while the skin owing to its elasticity can be stretched in different directions, which results in the skin marks not representing the original position in relation to the tumor.

One object of the present invention is to provide a positioning device having high accuracy in identifying the target area.

A further object of the invention is to provide a positioning device which permits reliable and repeatable identification of the treatment area.

According to the invention, these objects are achieved by a device as described by way of introduction, which is characterized in that the device comprises a non-yielding, upright and radioparent panel element and a base plate, which in a substantially perpendicular fashion is fixedly connected to said panel element, of which at least the panel element comprises fixation means for fixing the patient in a given, essentially upright orientation to the panel element, and that the device also comprises wheel means mounted on the base plate for moving the panel element and the patient to a radiotherapy table, a tilting and conveying assembly being arranged at the end of the table for tilting the panel element together with the patient from the upright orientation to a lying orientation and conveying these to a defined place on the table.

The invention is based on the knowledge that the skin is affected by gravity as the position of the body changes. The thicker the subcutaneous fat, the greater the movements. Also the patient's movement of hips and other parts of the body is difficult to reproduce by today's techniques.

The positioning problem is solved by carrying out the settings when the patient is placed in an upright position. When a person is standing without clothes and shoes, the skin costume will have a special carriage in relation to the skeleton. The legs have a given length and the hip-joints will have a position relative to the floor surface which is the same from occasion to occasion. The skin will be stretched owing to gravity, but this stretching will be the same from occasion to occasion during a radiotherapy period, unless an extreme loss of weight takes place.

The patient places himself on a base plate whose rear part is connected to an upright panel behind the patient's back. This panel should be made of a light-weight material since it is to form the base for the patient during radiotherapy. When the patient takes his natural upright position for the first time, considers that he is standing straight on the base plate and feels that his body reaches the panel behind his back in a resting fashion, correctly positioned relative to the panel, the skin is marked in a suitable position of the body by means of laser position lights or some other technique connected to the panel and indicating a relationship between the back panel and the body. It is the relationship of the body to the panel that is decisive of the continued positioning.

It should thus be possible to attach various means to the panel, which like building bricks can be snapped onto the panel on various levels, be removed after positioning or remain during computerized axial tomography, magnetic resonance imaging, stimulation work or during radiotherapy. This may involve positioning marks, lateral supports, supports for the curve of the back, head-neck, straps, masks and other fixation aids, connected to the panel.

After positioning of the patient, the panel should, with a satisfactory sense of security for the patient, slowly tilt the patient backwards to a recumbent position. The panel can advantageously be arranged at the end of the radiotherapy table, be tilted over the table in the longitudinal direction to a horizontal position on the wire-cloth of the table and subsequently be advanced along the table by means of the wire-cloth of the table. After treatment, the movements are reversed and the patient can leave.

What has been said about the patient's supine position also applies to all the other positions of the body sideways, lying on the face or any other position.

The panel concerned should also be designed to be possible to move like a "domestic baking plate" from computerized axial tomography to a treatment apparatus arranged on some carriage which readily enables moving of the patient without any efforts made by the staff. This confers the advantage that the patient can remain without changing the position of the body in connection with precision radiotherapy.

The panel should be fitted with or be fittable with supplementary aids to make it possible to position the panel by its own reference system in relation to equipment in a diagnostic clinic and radiotherapy clinic. In this context, reference is made to Swedish Patent 9302066 disclosing a stereotactical instrument having an orienting means which is suitable to mount on the panel.

The panel can also be fitted with electronic components such as transceivers, magnets, light sources etc. which can indicate the position in relation to the room and equipment of different types, the position of the patient, the position of the radiation fields on the patient and against the panel or the means of the panel.

What has been said about moving the patient between examination and treatment also applies to a preparatory positioning of the patient on the panel before the radiotherapy room is available, thereby gaining time for radiotherapy in case of limited radiotherapy capacity so as to increase the capacity.

Further it is possible to use more than one panel in one treatment session by one panel being arranged behind the patient and one panel with accessories being mounted in front of the patient in connection with radiotherapy.

What has been said about the panel does not necessarily signify a flat panel. It can also be shaped like a bucket seat, adapted completely to the contour of the patient, or it may have any appearance whatsoever.

A variant of the panel can be formed with a hinge in the center so as to permit the upper half to be pivoted upwards when treating breast cancer such that the breast-bone will be horizontally positioned, if desired.

BRIEF DESCRIPTION OF THE DRAWINGS

A preferred embodiment of the invention will now be described for the purpose of exemplification but not restriction, reference being made to the accompanying drawings, in which.

DETAILED DESCRIPTION

Figure 1:
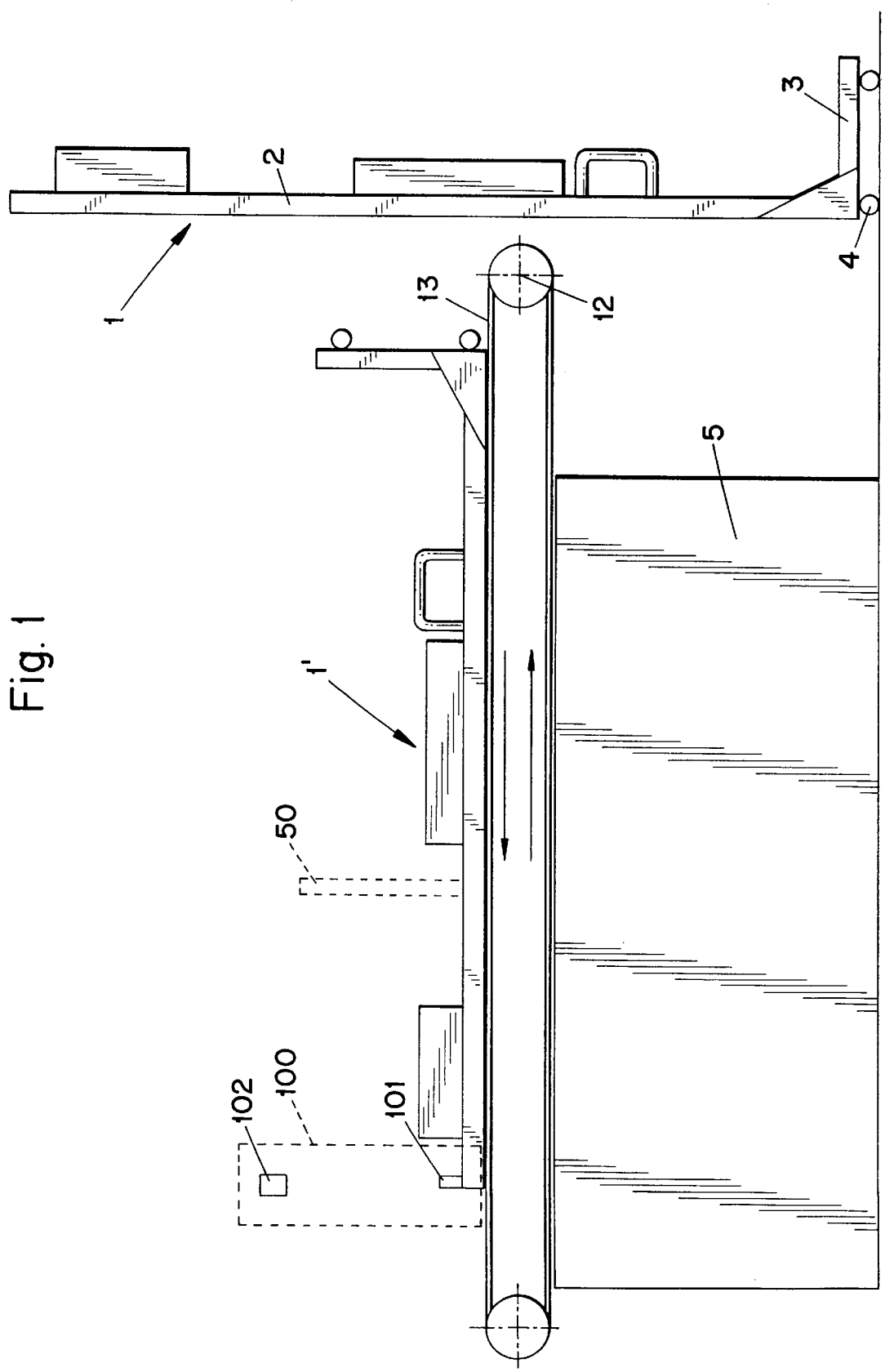
FIG. 1 is a schematic side view of the device according to the invention in a patient-fixing vertical orientation and a patient-positioning horizontal orientation respectively.

The inventive positioning device, which is generally designated 1 and 1' in the various figures, comprises a long narrow and non-yielding low-weight frame or panel element 2 which does not produce any obvious artifacts (disturbances) in the images, i.e. a material which is translucent to X-rays and other ionising radiation. A frame that can be used, for instance, in this context is illustrated in Swedish Patent 9302066. At one end of the panel element, a base plate 3 is fixedly arranged, substantially at right angles to the panel element 2. Preferably, wheel means 4, e.g. caster wheels, are arranged on the lower side of the base plate 3 to permit manual displacement to a radiotherapy table 5 of the positioning device 1 and a patient fixed to the positioning device. The wheel means are provided with a braking mechanism (not shown) to make the device 1, when fixing the patient to the panel element, stand steady on the floor. Optionally, a separate braking mechanism can be arranged on the base plate.

Figure 2:
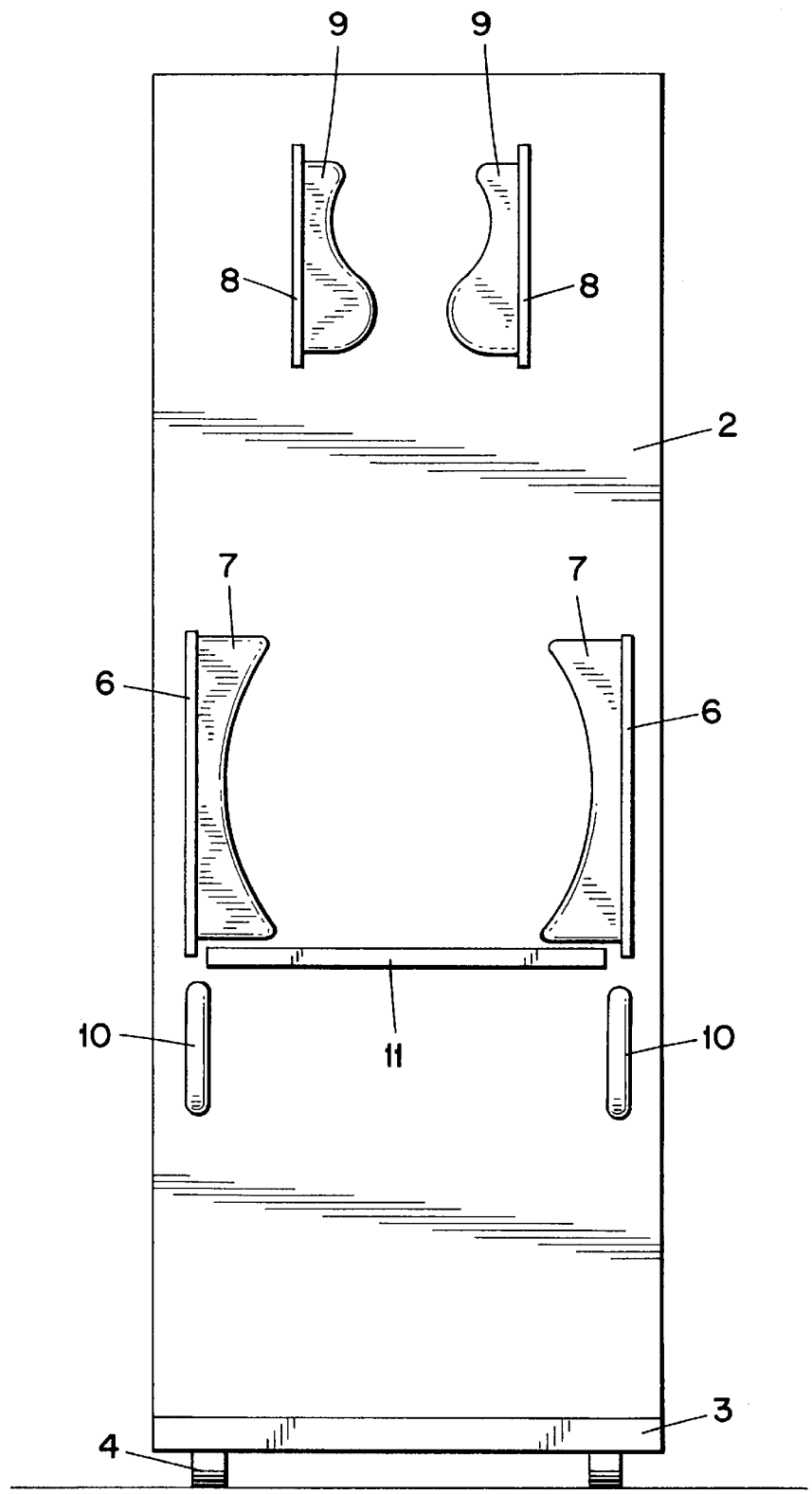
FIG. 2 is a front view of the device in FIG. 1 in a vertical orientation, the associated fixation means being indicated.

FIG. 2 illustrates schematically a fixation means for fixing a patient in an essentially upright position to the device 1. The fixation means comprises a hip support 6, which consists of a pair of essentially parallel, rigid flange components or the like projecting from an area at the long sides of the panel element 2. By means of exchangeable adjusting members 7, which are adapted to be arranged between the patient and the respective flange components, the hip portion of the patient can be fixed relative to the panel element. Before carrying out this fixing, the patient should, however, place his feet in the indicated positions, with or without guiding means, on the base plate 3. The fixation means may also comprise a head-neck support 8, which also consists of a pair of essentially parallel flange components or the like. Of course, the head-neck support is arranged closer to the vertical centre line of the panel element than the hip support and preferably coacts, like the hip support, with exchangeable adjusting members 9 positioned inside the head-neck support and serving to fix the patient's head relative to the panel element 2. The hip as well as head-neck supports can be fixedly arranged on the panel element, but preferably they can be snapped onto the panel element on different levels and in different positions in the lateral direction.

The positioning device can also be fitted with exchangeable lumbar supports, neckrests or other known molded components of light-weight material (not shown) for the purpose of positioning and/or for the sake of convenience. Preferably, the device comprises a pair of handles 10, which are arranged in a projecting fashion at the long sides of the panel element 2 below the hip support 6. The handles 10 serve to facilitate the fixing of the patient by his taking a steadier and straighter position when holding the handles. Moreover, the device 1 can be fitted with belts or straps 50 (shown in phantom in FIG. 1) and/or masks for fixing the patient more steadily to the panel element. Finally, the device can be provided with a seat 11 to be used by persons tied to their wheel chair or otherwise weak persons.

The panel element 2 has been described above as a straight element made in one piece. However, it may be shaped or divided and fitted with a horizontally oriented hinge (not shown) in the area between the hip support and the head-neck support for setting the panel element at an angle, for instance for breast cancer treatment. Alternatively, an additional angularly adjustable panel can be arranged on the panel element 2, or a separate insert, e.g. a wedge-shaped cushion, can be used. Also attachments for the positions of the arms can be fixed to the panel element.

When the patient has been fixed to the panel element as described above, this is moved together with the patient to the end of the radiotherapy table 5, see FIG. 1, is tilted over a guide roller 12 on the conveyor belt or wire-cloth 13 of the table and takes a horizontal position, as indicated by reference numeral 1'. The panel element 2 is fitted with setting means 100 (shown schematically in FIG. 1), for instance like the one disclosed in the above-mentioned Swedish Patent 9302066, or electronic components 101 such as transceivers, magnets, light sources etc. By means thereof, the panel element and, thus, the patient can be positioned with great accuracy on the treatment table or in the room in relation to the associated diagnostic or radiotherapy equipment 102 by means of the wire-cloth 13 or the movement of the table in the room.

Figure 3:
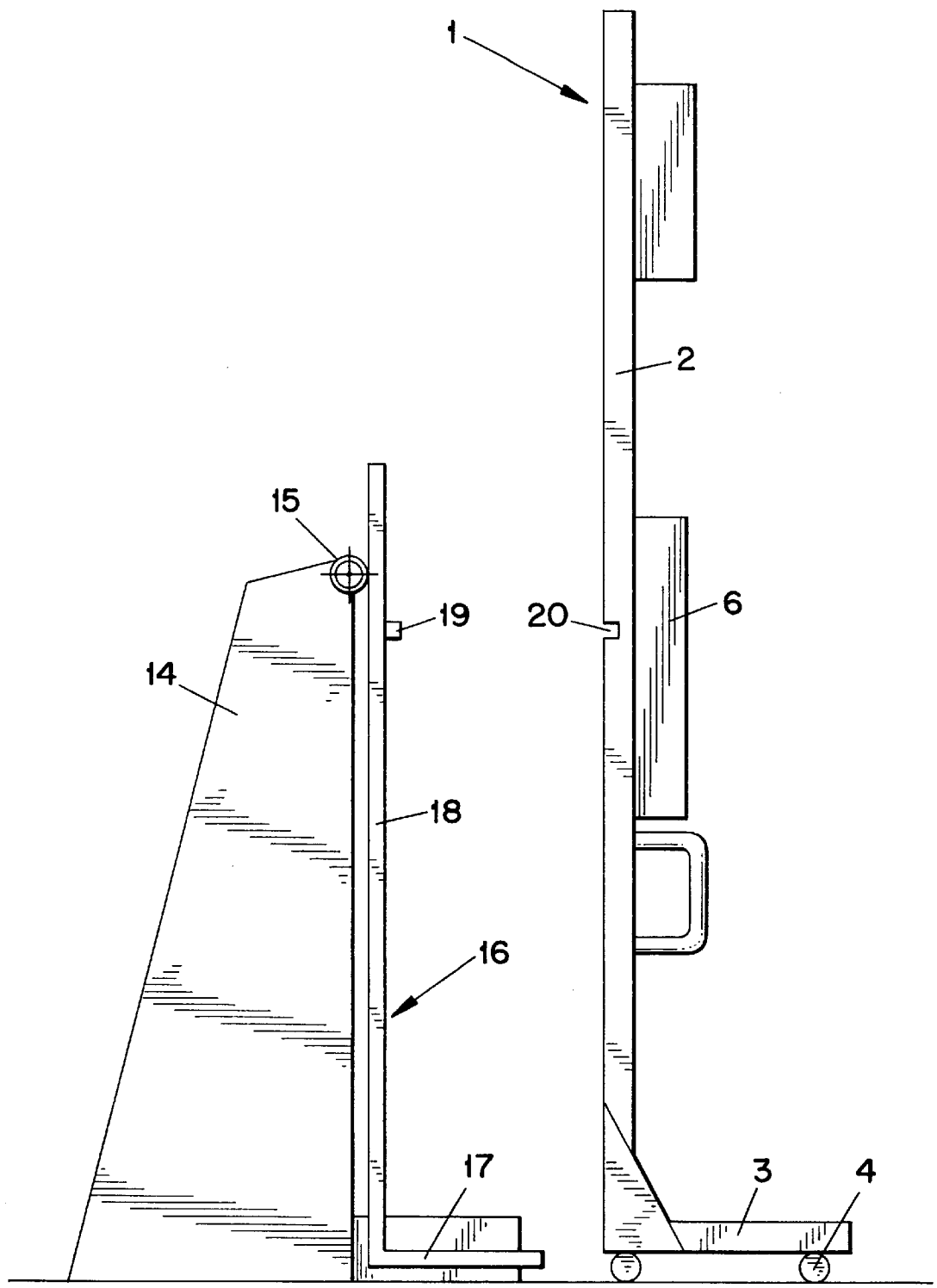
FIG. 3 shows on a larger scale a modified embodiment of the inventive device with an embodiment of an associated tilting assembly.

An assembly for facilitating the above-mentioned tilting of the device 1 is illustrated in FIG. 3. The tilting assembly comprises a stable foundation 14 which is arranged at the foot end of the treatment table 5 and whose upper portion is oriented on the same level as the treatment table. Optionally, the treatment table can be raised and lowered. A horizontal hinge 15 is arranged adjacent said portion and pivotally supports an L-shaped fork unit 16, on whose short, horizontal leg 17 the base plate 3 is adapted to be supported and against whose long, vertical leg 18 the panel element 2 is adapted to rest. A locking means 19, e.g. a pair of longitudinally displaceable pins, is arranged on the long leg 18, and a locking means 20, e.g. a pair of recesses, cooperating with the locking means 19, is arranged in the panel element 2. The locking means 19, 20 engage with each other during the tilting movement (from 1 to 1' in FIG. 1) in order to secure the device 1 to the fork unit 16 for the purpose of making the movement of the patient from the vertical to the horizontal position safe, and are disengaged from each other when the panel element rests on the wire-cloth 13.

The invention is not limited to that described above and shown in the drawings and can be modified within the scope of the claims.

I claim:

1. A device for repositioning a skeleton of a patient and an area of a body of the patient to be subjected to treatment, a position of the area in relation to the device having been previously determined the device comprising:
   a non-yielding, upright and radiolucent panel element;
   a base plate fixed substantially perpendicular to the panel element;
   at least the panel element including a fixation arrangement for fixing the patient in an essentially upright orientation relative to the panel element;
   wheels mounted on the base plate for moving the panel element and a patient mounted on the panel element to a radiotherapy table; and
   a tilting and conveying assembly adapted to be arranged at an end of the table for tilting the panel element together with the patient from the upright orientation to a lying orientation and for conveying the panel element and the patient to a defined place on the table.

2. The device as claimed in claim 1, wherein the fixation arrangement includes a hip support, the hip support including a pair of essentially parallel, rigid flange components projecting from sides of the panel element and coacting with adjusting members inside the hip support, the fixation arrangement being adapted to position and fix a hip portion of the patient relative to the panel element.

3. The device as claimed in claim 2, wherein the fixation arrangement includes a head-neck support, the head-neck support including a pair of essentially parallel, rigid and releasable flange components projecting from a central portion of the panel element and coacting with adjusting members inside the head-neck support, the fixation arrangement being adapted to fix a head of the patient relative to the panel element.

4. The device as claimed in claim 1, wherein the fixation arrangement includes fastening straps or bands arranged to extend transversely across the panel element, the fastening straps or bands being adapted to urge the patient against the panel element.

5. The device as claimed in claim 1, further comprising a pair of handle components, the pair of handle components projecting from sides of the panel element.

6. The device as claimed in claim 1, wherein the device includes a seat component, the seat component being releasably arranged on the panel element, the seat component being adapted to serve as a seat for the patient.

7. The device as claimed in claim 1, wherein a first locking device is arranged on the panel element and cooperates with a second locking device provided on the tilting and conveying assembly, the tilting and conveying assembly including a foundation having an upper portion, the upper portion being adapted to be oriented on a level of the radiotherapy table, the upper portion having a hinge, the tilting and conveying assembly including a fork unit pivotally attached to the hinge, the second locking device being arranged on the fork unit.

8. The device as claimed in claim 1, further comprising a setting arrangement for positioning and indicating a position of the panel element on the radiotherapy table in relation to surrounding structures.

9. The device as claimed in claim 2, wherein the fixation arrangement includes fastening straps or bands arranged to extend transversely across the panel element, the fastening straps or bands being adapted to urge the patient against the panel element.

10. The device as claimed in claim 3, wherein the fixation arrangement includes fastening straps or bands arranged to extend transversely across the panel element, the fastening straps or bands being adapted to urge the patient against the panel element.

11. The device as claimed in claim 2, further comprising a pair of handle components, the pair of handle components projecting from sides of the panel element.

12. The device as claimed in claim 3, further comprising a pair of handle components, the pair of handle components projecting from sides of the panel element.

13. The device as claimed in claim 4, further comprising a pair of handle components, the pair of handle components projecting from sides of the panel element.

14. The device as claimed in claim 2, wherein the device includes a seat component, the seat component being releasably arranged on the panel element, the seat component being adapted to serve as a seat for the patient.

15. The device as claimed in claim 3, wherein the device includes a seat component, the seat component being releasably arranged on the panel element, the seat component being adapted to serve as a seat for the patient.

16. The device as claimed in claim 2, wherein a first locking device is arranged on the panel element and cooperates with a second locking device provided on the tilting and conveying assembly, the tilting and conveying assembly including a foundation having an upper portion, the upper portion being adapted to be oriented on a level of the radiotherapy table, the upper portion having a hinge, the tilting and conveying assembly including a fork unit pivotally attached to the hinge, the second locking device being arranged on the fork unit.

17. The device as claimed in claim 3, wherein a first locking device is arranged on the panel element and cooperates with a second locking device provided on the tilting and conveying assembly, the tilting and conveying assembly including a foundation having an upper portion, the upper portion being adapted to be oriented on a level of the radiotherapy table, the upper portion having a hinge, the tilting and conveying assembly including a fork unit pivotally attached to the hinge, the second locking device being arranged on the fork unit.

18. The device as claimed in claim 2, further comprising a setting arrangement for positioning and indicating a position of the panel element on the radiotherapy table in relation to surrounding structures.

* * * * *